(12) United States Patent
Schultz et al.

(10) Patent No.: US 6,194,395 B1
(45) Date of Patent: Feb. 27, 2001

(54) CYCLODEXTRIN CLADRIBINE FORMULATIONS

(75) Inventors: Thomas W. Schultz, Richboro, PA (US); Rainer Naeff, Langwiesen (CH)

(73) Assignee: Orthro-McNeil Pharmaceutical, Inc., Raritan, NJ (US)

(*) Notice: Subject to any disclaimer, the term of this patent is extended or adjusted under 35 U.S.C. 154(b) by 0 days.

(21) Appl. No.: 09/257,809

(22) Filed: Feb. 25, 1999

(51) Int. Cl.⁷ .................. A01N 43/04; A01N 43/90; A61K 31/715; A61K 31/52

(52) U.S. Cl. .................................. 514/58; 514/266

(58) Field of Search ....................... 514/266, 58

(56) References Cited

U.S. PATENT DOCUMENTS

| 4,719,295 | * | 1/1988 | Cook et al. | 536/26 |
| 4,727,064 | * | 2/1988 | Pitha | 514/58 |
| 4,764,604 | | 8/1988 | Muller | 536/103 |
| 5,641,757 | | 6/1997 | Bornstein et al. | 514/46 |
| 5,681,822 | * | 10/1997 | Bornstein et al. | 514/46 |

FOREIGN PATENT DOCUMENTS

WO 97/18839   11/1996   (EP).

* cited by examiner

Primary Examiner—Dwayne C. Jones
(74) Attorney, Agent, or Firm—Kenneth J. Dow

(57) ABSTRACT

There is provided by the present invention liquid injectable and oral solid pharmaceutical dosage forms containing a mixture of cladribine (2-chloro-2'-deoxyadenosine; 2-CdA) and cyclodextrin.

14 Claims, 1 Drawing Sheet

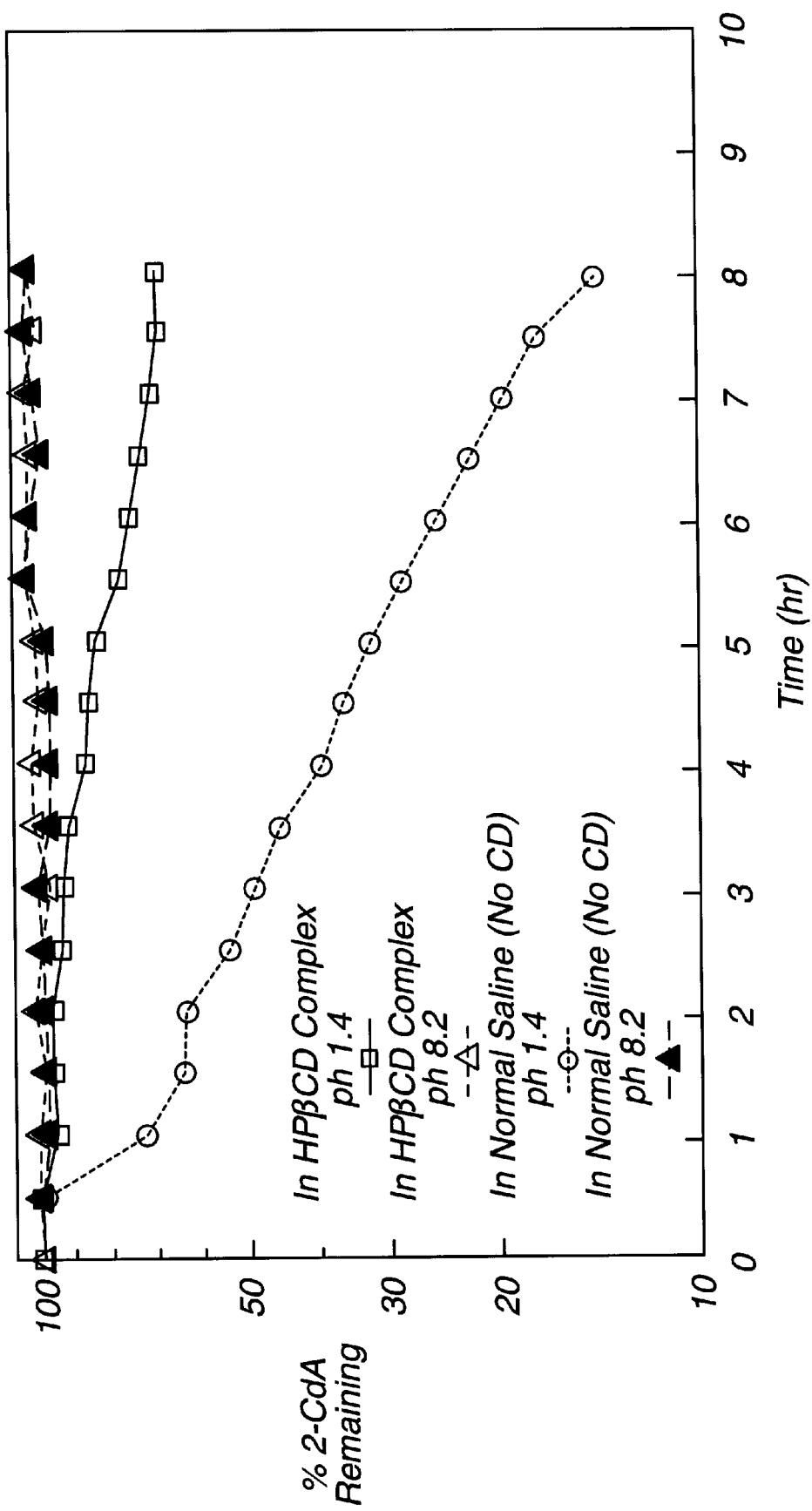

CYCLODEXTRIN CLADRIBINE FORMULATIONS

This invention relates to pharmaceutically useful cyclodextrin formulations of cladribine (2-chloro-2'-deoxyadenosine; 2-CdA). More particularly, this invention relates to soluble aqueous formulations of cladribine with cyclodextrin solubilizers which are injectable in humans, as well as oral solid dosage forms containing a mixture of cladribine and cyclodextrins.

BACKGROUND OF THE INVENTION

The compound cladribine has the following formula:

Cladribine is known as an antileukemic agent, i.e., in treating leukemias, such as, hairy cell leukemia and L 1210 leukemia, and as an immunosuppressive agent (D. A. Carson, D. Bruce Wasson, and Ernest Beutler, Proc. Soc. Acad. Sci. USA, Vol. 81, pp 2232–2236, 1984). More recently, cladribine has been disclosed as effective in the treatment of rheumatoid arthritis and multiple sclerosis, U.S. Pat. No. 5,310,732.

To date, cladribine has been administered by intravenous injection of saline solutions presenting two problems for subcutaneous or intramuscular injection. First, cladribine is slightly soluble in water which requires a large volume of material to be injected subcutaneously or intramuscularly to achieve the required dose. Dilute solutions are acceptable for intravenous injection, but may create pain or inflammatory difficulties for subcutaneous or intramuscular injection. Secondly, cladribine has limited stability in simple saline solutions. Stability of the compound is hampered by its tendency to undergo hydrolysis, particularly under acidic conditions. Longer shelf-life is beneficial for extended storage at refrigerated or room temperature conditions. Use of the compound orally has been limited by the fact that cladribine is acid labile and would not be stable in the acidic environment of the gastro-intestinal system.

U.S. Pat. No. 5,310,732, col. 8. teaches a 0.1 mg/mL isotonic saline solution of cladribine. There has been marketed a non-buffered solution containing 1.0 mg/mL of cladribine in 9.0 mg/mL Sodium Chloride Injection, USP.

U.S. Pat. Nos. 5,641,757 and 5,681,822 describe injectable aqueous formulations of cladribine in which the active cladribine material is solubilized with a cosolvent mixture of benzyl alcohol and propylene glycol and stabilized with m-cresol as a preservative. Use of the cosolvent mixtures disclosed therein enabled aqueous formulations of 2 to about 8 mg/ml cladribine. However, the disadvantage of these formulations lies in the danger of supersaturation and the very high osmolality of the solution. The osmolality is between 1000 and 2000 mosm while physiological osmolality is around 290 mosm. The high osmolality may result in pain and irritation when injected by the subcutaneous route. Recrystallisation of cladribine in the tissue may occur and damage the surrounding tissue.

Thus, there is a need for new formulations of cladribine which allow the subcutaneous or intramuscular injection of more concentrated aqueous solutions of cladribine which are isotonic and isohydric. Further, there is a need for oral formulations of cladribine which are stable against hydrolysis, particularly in an acid environment.

β-cyclodextrin is a cyclic compound consisting of seven units of α-(1→4) linked D-gluco-pyranose units and is known as a complexing agent. Cyclodextrins are known in the art to possess the ability to form inclusion complexes and to have concomitant solubilizing properties. The properties of cyclodextrins and their properties have been reviewed in detail [see Szejtli, J. Cyclodextrin technology, (1988) Kluwer Academic Publishers, Dordrecht].

BRIEF DESCRIPTION OF THE DRAWINGS

FIG. 1 shows the effect of hydroxypropyl-β-cyclodextrin on the stability of cladribine at pH 1.4

SUMMARY OF THE INVENTION

There is provided by the present invention a solution of cladribine in water comprising:

a) from about 1 to about 15 mg/mL of cladribine or its pharmaceutically acceptable salts; and b) from about 1 to about 350 mg/ml cyclodextrin solubilizing agent.

In a further aspect of the invention, there is provided a solid pharmaceutical oral dosage form of cladribine comprising:

a) from about 1 to about 15 mg cladribine or its pharmaceutically acceptable salts; and b) from about 100 to about 500 mg of a cyclodextrin; in association with one or more pharmaceutically acceptable carriers.

DETAILED DESCRIPTION OF THE INVENTION

Processes for preparing cladribine are known. European Patent Application No. 173,059 A2 and Robins et al., J. Am. Chem. Soc., 106, 6379(1984) disclose the preparation or cladribine. The preparation consists of the glycosylation of 2,6-dichloropurine with 1-chloro-2'-deoxy-3',5'-di-O-p-toluoyl-b-D-erythropentofuranose to yield the N-9 glycosylated purine, 2,6-dichloro-9-deoxy-3, 5-di-0-p-toluoyl-b-D-erythropentofuranosyl) -purine. which is subsequently reacted with ammonia to yield cladribine. An alternative method to manufacture cladribine is taught in U.S. Pat. No. 5,208,327 by Robert H. K. Chen.

As the cyclodextrin in the compositions of the invention, there may be used any of the physiologically tolerable water-soluble substituted or unsubstituted cyclodextrins or physiologically tolerable derivatives thereof, e.g. α-, β- or γ-cyclodextrins or derivatives thereof, in particular derivatives wherein one or more of the hydroxy groups are substituted, e.g. by alkyl, hydroxyalkyl, carboxyalkyl, alkylcarbonyl, carboxyalkoxyalkyl, alkylcarbonyloxyalkyl, alkoxycarbonylalkyl or hydroxy-(mono or polyalkoxy)alkyl groups, wherein each alkyl or alkylene moiety preferably contains up to six carbons.

Substituted cyclodextrins which can be used in the invention include polyethers, e.g. as described in U.S. Pat. No. 3,459,731. In general, to produce these, unsubstituted cyclodextrins are reacted with an alkylene oxide, preferably under superatmospheric pressure and at an elevated temperature, in the presence of an alkaline catalyst. Since a hydroxy moiety of the cyclodextrin can be substituted by an alkylene oxide which itself can react with yet another molecule of alkylene oxide, the average molar substitution (MS) is used as a measure of the average number of moles of the substituting agent per glucose unit. The MS can be greater than 3 and theoretically has no limit. In the cyclodextrin derivatives for use in the compositions according to the present invention the M.S is conveniently in the range of 0.125 to 10, in particular of 0.3 to 3, or from 0.3 to 1.5. Preferably the M.S. ranges from about 0.3 to about 0.8, in particular from about 0.35 to about 0.5 and most particularly it is about 0.4. M.S. values determined by NMR or IR preferably range from 0.3 to 1, in particular from 0.55 to 0.75.

Further examples of substituted cyclodextrins include ethers wherein the hydrogen of one or more cyclodextrin hydroxy groups is replaced by $C_{1-6}$alkyl, hydroxy$C_{1-6}$-alkyl, carboxy-$C_{1-6}$alkyl or $C_{1-6}$alkyloxycarbonyl-$C_{1-6}$alkyl groups or mixed ethers thereof. In particular such substituted cyclodextrins are ethers wherein the hydrogen of one or more cyclodextrin hydroxy groups is replaced by $C_{1-3}$alkyl, hydroxy-$C_{2-4}$alkyl or carboxy-$C_{1-2}$alkyl or more particularly by methyl, ethyl, hydroxyethyl, hydroxypropyl, hydroxybutyl, carboxymethyl or carboxyethyl.

In the foregoing definitions, the term "$C_{1-6}$alkyl" is meant to include straight and branched saturated hydrocarbon radicals, having from 1 to 6 carbon atoms, such as methyl, ethyl 1-methylethyl, 1,1-dimethylethyl, propyl, 2-methylpropyl, butyl, pentyl, hexyl and the like.

Such ethers can be prepared by reacting a cyclodextrin with an appropriate O-alkylating agent or a mixture of such agents in a concentration selected such that the desired cyclodextrin ether is obtained. The reaction is preferably conducted in a solvent in the presence of a base. With such ethers, the degree of substitution (DS) is the average number of substituted hydroxy functions per glucose unit, the DS being thus 3 or less.

In the cyclodextrin derivatives for use in the compositions according to the present invention, the DS preferably is in the range of 0.125 to 3, in particular 0.3 to 2, more particularly 0.3 to 1, and the MS is in the range of 0.125 to 10, in particular 0.3 to 3 and more particularly 0.3 to 1.5.

Of particular utility in the present invention are the β-cyclodextrin ethers, e.g. dimethyl-β-cyclodextrin as described in Drugs of the Future, Vol. 9, No. 8, p. 577–578 by M. Nogradi (1984) and polyethers, e.g. hydroxypropyl-p-cyclodextrin and hydroxyethyl-β-cyclodextrin. Such alkyl ethers may for example be methyl ethers with a degree of substitution of about 0.125 to 3, e.g. about 0.3 to 2. Such a hydroxypropyl cyclodextrin may for example be formed from the reaction between β-cyclodextrin and propylene oxide and may have a MS value of about 0.125 to 10, e.g. about 0.3 to 3.

Especially suitable cyclodextrins are β-CD, 2,6-dimethyl-P-CD, 2-hydroxyethyl-β-CD, 2-hydroxyethyl-β-CD, 2-hydroxypropyl-β-CD and (2-carboxymethoxy)propyl-β-CD, and in particular 2-hydroxypropyl-β-CD.

Besides simple cyclodextrins, branched cyclodextrins and cyclodextrin polymers may also be used.

Other cyclodextrins are described for example in Chemical and Pharmaceutical Bulletin 28: 1552–1558 (1980), Yakugyo Jiho No. 6452 (28 March 1983), Angew. Chem. Int. Ed. Engl. 19: 344–362 (1980), U.S. Pat. No. 3,459,731, EP-A-0,149,197, EP-A-0,197,571, U.S. Pat. No. 4,535,152, WO-90/12035 and GB-2,189,245. Other references describing cyclodextrins for use in the compositions according to the present invention, and which provide a guide for the preparation, purification and analysis of cyclodextrins include the following: "Cyclodextrin Technology" by József Szejtli, Kluwer Academic Publishers (1988) in the chapter Cyclodextrins in Pharmaceuticals; "Cyclodextrin Chemistry" by M. L. Bender et al., Springer-Verlag, Berlin (1978); "Advances in Carbohydrate Chemistry", Vol. 12, Ed. by M. L. Wolfrom, Academic Press, New York in the chapter The Schardinger Dextrins by Dexter French at p. 189–260; "Cyclodextrins and their Inclusion Complexes" by J. Szejtli, Akademiai Kiado, Budapest, Hungary (1982); I. Tabushi in Acc. Chem. Research, 1982, 15, p. 66–72; W. Sanger, Angewandte Chemie, 92, p. 343–361 (1981); A. P. Croft and R. A. Bartsch in Tetrahedron, 39, p. 1417–1474 (1983); Irie et al. Pharmaceutical Research, 5, p. 713–716, (1988); Pitha et al. Int. J. Pharm. 29, 73, (1986); DE 3,118,218; DE-3, 317,064; EP-A-94,157; U.S. Pat. No. 4,659,696; and U.S. Pat. No. 4,383,992.

More recent examples of substituted cyclodextrins include sulfobutylcyclodextrins (U.S. Pat. No. 5,134,127-A). Their use is also envisaged in the present invention.

The cyclodextrin used is preferably a β-cyclodextrin, in particular hydroxypropyl-β-cyclodextrin. The most preferred cyclodextrin derivative for use in the compositions of the present invention is hydroxypropyl-β-cyclodextrin having a M.S. in the range of from 0.35 to 0.50 and containing less than 1.5% unsubstituted β-cyclodextrin. M.S. values determined by NMR or IR preferably range from 0.55 to 0.75.

The liquid dosage form contains from about 1 to about 15 mg/mL of cladribine or its pharmaceutically acceptable salts, preferably from about 5 to about 12 mg/ml, most preferably about 10 mg/ml. The cyclodextrin is generally present in an amount necessary to solubilize the cladribine, i.e., from about 1 to about 350 mg/ml, preferably from about 200–300 mg/ml. The amount of cyclodextrin should be tailored to produce an isotonic and isohydric solution, generally in the range of about 20% of the composition. The combination of cladribine and cyclodextrin in this concentration, preferably HPCD, results in a colorless, isotonic and isohydric solution.

Alternatively, sufficient sodium chloride can be added to the solution to render it isotonic.

The liquid dosage form may also optionally contain a pharmaceutically acceptable buffer to maintain the pH at a range of about 5.5 to about 8.5. The preferred pH range for shelf stable solutions is about 6.0 and 8.0. Suitable buffers are any of those available for pharmaceutical application. Such buffers include but are not limited to phosphate, citrate, acetate, borate and tris. The preferred buffer for use herein is a sodium phosphate buffer system containing a mixture of monobasic sodium dihydrogenphosphate dihydrate and dibasic di-sodium hydrogenphosphate dihydrate. The ratio of phosphate buffers is adjusted to achieve the pH desired, generally in about a 2 to 1 monobasic to dibasic phosphate buffer ratio. The amount of buffer generally range from about 0 to about 12 mg/ml monobasic phosphate buffer and about 0 to about 24 mg/ml dibasic phosphate buffer.

The liquid dosage form may also optionally contain a preservative to prevent antimicrobial contamination. If employed, the preservative component may be selected from any pharmaceutically acceptable preservative. M-cresol may be used as well as the alkyl esters of parahydroxybenzoic acid (the parabens, e.g. butylparaben, methylparaben and propylparaben), alone or in combination. Generally, the preservatives are used in a concentration of about 0.02% w/v. Other preservatives include ethylenediamine tetra-acetic acid, propyl-p-hydroxybenzoates or sorbic acid.

By employing the cyclodextrin liquid formulations of the present invention, the solubility of cladribine can be significantly enhanced. In this manner the injection volume can be reduced to less than 1 ml per injection. Irritation and pain due to high osmolality or large injection volumes can thus be reduced. In addition, cladribine is significantly more stable at lower pH when combined with cyclodextrins like HPCD.

Further, due to the small volumes (0.5–1 ml) that can be achieved using the cyclodextrin liquid dosage forms of the present invention, patient friendly applicators or drug delivery devices such as auto-injectors or pen injectors can be employed for subcutaneous administration of cladribine.

A typical liquid formulation of the present invention may for example comprise the following composition:

| | |
|---|---|
| Cladribine | 1.0–15.0 mg/ml |
| 2-Hyroxypropyl-β-Cyclodextrin (parenteral grade) | 1.0–350.0 mg/ml |
| Sodium Dihydrogenphosphate Dihydrate | 0.0–24 mg/ml |
| di-Sodium Hydrogenphosphate Dihydrate | 0.0–48 mg/ml |
| Water for Injection | ad 100.0 |

The use of the cyclodextrin formulations of the present invention also provide an additional benefit in that it has been found that cladribine is significantly more stable against hydrolysis when combined with cyclodextrins. This is of particular benefit in the formulation of solid oral dosage forms, where the compound would normally undergo hydrolysis in the acid pH of the stomach contents. However, as shown in FIG. 1, the stability of cladribine at pH 1.4 is significantly enhanced when combined with cyclodextrins.

The solid oral dosage forms of the present invention may be prepared in the form of tablets, caplets, gelcaps, capsules, chewable tablets, lozenges, fast dissolving wafers, and other known and effective delivery modes. The cladribine/cyclodextrin composition may be admixed with a variety of pharmaceutically acceptable excipients including fillers, binders, sweeteners, artificial sweeteners, lubricants, glidants, disintegrants, colors, adsorbents, acidifying agents, and flavoring agents. The choice of excipient will depend on the solid oral dosage form employed (i.e. tablets, caplets, or capsules) and whether the dosage form is chewable or a swallowable formulation. Swallowable oral tablets are preferred.

One method of preparing the solid oral dosage forms is disclosed in patent application WO97/18839, hereby incorporated by reference. In this method, solid mixtures of the cyclodextrins with the active ingredient are prepared via melt-extrusion, where the active ingredient is embedded in the cyclodextrin carrier. In accordance with this technique, the cladribine active ingredient and the cyclodextrins are mixed with other optional additives and then heated until melting occurs. The mixture is then extruded through an extruder having one or more nozzles. The resulting mass is then cooled and prepared into pellets which can be used to prepare conventional solid pharmaceutical dosage forms. In doing so, the extrudate may be admixed with various excipients commenly used in pharmaceutical tablets and coated in an art-known way.

For example, suitable tablets may be prepared in the conventional way having one or more of the following excipients:

a) diluents such as lactose, kaolin, mannitol, crystalline sorbitol, talc and the like;

b) binders such as sugars, microcrystalline cellulose, alginic acid, carboxymethyl cellulose, croscarmellose sodium, polyvinylpyrrolidone, crospovidone and the like;

c) lubricants such as magnesium stearate, talc, calcium stearate, zinc stearate, stearic acid, hydrogenated vegetable oil, leucine, glycerides and sodium stearyl fumarate;

d) disintegrants such as starches, methylcellulose, agar, bentonite, alginic acid, carboxymethylcellulose, polyvinylpyrrolidone and the like;

e) scavengers such as silicon dioxide;

f) flavoring agents such as mannitol, dextrose, fructose, sorbitol and the like; and g) coloring agents.

Other suitable excipients can be found in the Handbook of Pharmaceutical Excipients, published by the American Pharmaceutical Association, herein incorporated by reference.

A typical oral dosage form of the present invention may have a formulation containing various components in accordance with the following:

Milled extrudate

| | |
|---|---|
| Cladribine | 1 mg to 15 mg |
| Cyclodextrin | 100 to 500 mg |

Excipients

| | |
|---|---|
| Microcrystalline cellulose | 100 to 300 mg |
| Crospovidone | 10 to 200 mg |
| Colloidal silicon dioxide | 1 to 5 mg |
| Sterotex | 2 to 10 mg. |

The cladribine/cyclodextrin formulation of the present invention is useful as an oral or parenteral formulation as a neoplastic in treating leukemias such as hairy cell leukemia and chronic myelogenous leukemia. It may also have application in the treatment of a variety of disease states and autoimmune disorders such as multiple sclerosis, autohemolytic anemia, inflammatory bowel disease, rheumatoid arthritis, malignant astrocytoma and the like. Effective dosages are expected to vary considerably depending on the condition being treated and the route of administration. For treating hairy cell leukemia, the dosage is 0.09 mg/kg/day for 7 days. For treatment of multiple sclerosis the dosage can range from about 0.04 to about 1.0 mglkg of body weight per day, preferably from about 0.05 to about 0.15 mg/kg/day, as described in U.S. Pat. No. 5,506,214. Preferable doses for treatment of other disorders are described in U.S. Pat. Nos. 5,106,837, 5,506,213, 5,310,732, 5,401,724 and 5,424,296.

The invention is illustrated, but in no way limited, by the following examples.

EXAMPLE 1

The formulation of Table 1 was prepared and found to be suitable for use as an injectable and pharmaceutically useful solution. The pH of the solution is about 7.3.

Table 1

Composition: (mg/ml)

TABLE 1

| Composition: (mg/ml) | |
| --- | --- |
| Cladribine | 10.0 |
| 2-Hyroxypropyl-β-Cyclodextrin (parenteral grade) | 275.0 |
| Sodium Dihydrogenphosphate Dihydrate | 1.2 |
| di-Sodium Hydrogenphosphate Dihydrate | 2.4 |
| Water for Injection | 797.5 |

Procedure:

The cylodextrin and the buffer salts were solved in Water for Injection and an excess of Cladribine was added. The solution was shaken during 5 days at room temperature and 4° C. The solution was filtered through a 0.2 µm filter.

EXAMPLE 2

The solubility of cladribine in water at various concentrations of 2-Hydroxypropyl-β-Cyclodextrin (HPCD) was measured by high performance liquid chromatography. The normal solubility of cladribine in water is about 4.52 mg/ml. Table 2 sets forth the results of the solubility measurements for the HPCD/cladribine formulation of Example 1.

TABLE 2

| % HP-β-CD (W/W) | pH | Solubility of Cladribine at 4° C. |
| --- | --- | --- |
| 10 | 7.3 | 4.93 |
| 15 | 7.3 | 6.51 |
| 20 | 7.3 | 8.27 |
| 25 | 7.3 | 9.91 |

| % HP-β-CD (W/W) | pH | Solubility of Cladribine (mg/ml) at RT |
| --- | --- | --- |
| 10 | 7.3 | 6.4 |
| 15 | 7.3 | 8.47 |
| 20 | 7.3 | 10.48 |
| 25 | 7.3 | 12.36 |

The foregoing results demonstrate a greatly increased solubility of cladribine in water through use of the cyclodextrin formulation of the present invention.

EXAMPLE 3

A solution of 10 mg/ml cladribine in 20% HPCD was prepared by heating the mixture to 80° C. for 5 minutes. A complex of caldribine/HPCD is formed at a 1:1.5 molar ratio. The effect of the HPCD on the stability of cladribine at pH 1.4 and 8.2 at room temperature was measured. The results are shown in FIG. 1.

As shown in FIG. 1, the cladribine/EPCD complex was significantly more stable at pH 1.4 than the cladribine solution prepared without HPCD.

We claim:

1. A solution of cladribine in water comprising:
   a) from about 1 to about 15 mg/mL of cladribine or its pharmaceutically acceptable salts; and
   b) from about 1 to about 350 mg/ml cyclodextrin solubilizing agent.

2. The solution of claim 1 wherein the cyclodextrin is selected from an α-cyclodextrin, a β-cyclodextrin, a γ-cyclodextrin, and a derivative thereof.

3. The solution of claim 1 wherein the cyclodextrin is selected from 2-Hydroxypropyl-β-Cyclodextrin.

4. The solution of claim 1 comprising about 5 to about 12 mg/ml cladribine.

5. The solution of claim 1 comprising about 10 mg/ml cladribine.

6. The solution of claim 1 comprising about 20% w/v 2-Hydroxypropyl-β-Cyclodextrin.

7. The solution of claim 1 comprising the following formula:

| Composition: (mg/ml) | |
| --- | --- |
| Cladribine | 10.0 |
| 2-Hyroxypropyl-β-Cyclodextrin (parenteral grade) | 275.0 |
| Sodium Dihydrogenphosphate Dihydrate | 1.2 |
| di-Sodium Hydrogenphosphate Dihydrate | 2.4 |
| Water for Injection. | 797.5. |

8. A solid pharmaceutical oral dosage form of cladribine comprising:
   a) from about 1 to about 15 mg cladribine or its pharmaceutically acceptable salts; and
   b) from about 100 mg to about 500 mg of a cyclodextrin;
   in association with one or more pharmaceutically acceptable carriers.

9. The composition of claim 8 wherein the cyclodextrin is selected from an α-cyclodextrin, a β-cyclodextrin, a γ-cyclodextrin, and a derivative thereof.

10. The composition of claim 8 wherein the cyclodextrin is selected from 2-Hydroxypropyl-β-Cyclodextrin.

11. The composition of claim 8 comprising about 5 to about 15 mg cladribine.

12. The composition of claim 8 comprising about 10 mg cladribine.

13. The composition according to claim 8 prepared by melt-extrusion, where the cladribine is embedded in a cyclodextrin carrier.

14. A solid composition according to claim 8 prepared by melt-extrusion having the following formula:

Milled Extrudate

| | |
| --- | --- |
| Cladribine | 1 mg to 15 mg |
| Cyclodextrin | 100 mg to 500 mg |

Excipients

| | |
| --- | --- |
| Microcrysstalline Cellulose | 100 mg to 200 mg |
| Crospovidone Binders | 10 mg to 200 mg |
| Colloidal Silicone Dioxide | 1 mg to 5 mg |
| Sterotex | 2 mg to 10 mg. |

* * * * *